(12) United States Patent
Dupuy

(10) Patent No.: US 11,718,571 B2
(45) Date of Patent: *Aug. 8, 2023

(54) EMOLLIENT COMPOSITION

(71) Applicant: TOTAL MARKETING SERVICES, Puteaux (FR)

(72) Inventor: Carole Dupuy, Issy les Moulineaux (FR)

(73) Assignee: TOTAL MARKETING SERVICES, Puteaux (FR)

( * ) Notice: Subject to any disclaimer, the term of this patent is extended or adjusted under 35 U.S.C. 154(b) by 0 days.

This patent is subject to a terminal disclaimer.

(21) Appl. No.: 17/839,156

(22) Filed: Jun. 13, 2022

(65) Prior Publication Data

US 2022/0306551 A1    Sep. 29, 2022

Related U.S. Application Data

(62) Division of application No. 16/481,017, filed as application No. PCT/EP2018/053472 on Feb. 13, 2018, now abandoned.

(30) Foreign Application Priority Data

Feb. 13, 2017   (EP) ..................... 17155898

(51) Int. Cl.
| | |
|---|---|
| *C07C 5/03* | (2006.01) |
| *C07C 7/04* | (2006.01) |
| *A61K 8/31* | (2006.01) |
| *A61K 31/01* | (2006.01) |
| *A61K 8/06* | (2006.01) |
| *A61Q 19/00* | (2006.01) |
| *C07C 9/16* | (2006.01) |

(52) U.S. Cl.
CPC ............. *C07C 5/03* (2013.01); *A61K 8/31* (2013.01); *A61K 31/01* (2013.01); *C07C 7/04* (2013.01); *A61K 8/062* (2013.01); *A61K 8/064* (2013.01); *A61K 8/066* (2013.01); *A61Q 19/00* (2013.01); *C07C 9/16* (2013.01)

(58) Field of Classification Search
None
See application file for complete search history.

(56) References Cited

U.S. PATENT DOCUMENTS

| | | |
|---|---|---|
| 5,800,816 A | 9/1998 | Brieva et al. |
| 5,882,663 A | 3/1999 | Koeniger et al. |
| 9,688,924 B2 | 6/2017 | Dalemat et al. |
| 2005/0080304 A1 | 4/2005 | Lehtonen et al. |
| 2005/0288471 A1 | 12/2005 | Bitterlich et al. |
| 2008/0193404 A1 | 8/2008 | Lange |
| 2012/0264656 A1 | 10/2012 | Germanaud |
| 2016/0289573 A1 | 10/2016 | Dupuy |
| 2016/0312131 A1 | 10/2016 | Luebke |
| 2018/0148656 A1 | 5/2018 | Germanaud et al. |
| 2018/0155636 A1 | 6/2018 | Germanaud et al. |
| 2018/0193404 A1 | 7/2018 | Brown |

FOREIGN PATENT DOCUMENTS

| | | |
|---|---|---|
| DE | 102004018752 | 11/2005 |
| PL | 199805 B1 * | 11/2008 |
| WO | 2013/093227 | 6/2013 |

OTHER PUBLICATIONS

English Machine Translation PL 199805. Obtained May 25, 2022 (Year: 2022).*
English translation of DE102004018752 obtained from Espacenet, pp. 1-11 (Year: 2020).
Wilbur Johnson et al, "Safety Assessment of Isoparaffins as Used in Cosmetics", International Journal of Toxicology, US, (2012), vol. 31, No. 6_suppl, p. 269S-p. 273S.
Wypych, G., "Isododecane" Knovel Solvents—A Properties Database. 2008, p. 1-2 (Year: 2008).

* cited by examiner

*Primary Examiner* — Philip Y Louie
(74) *Attorney, Agent, or Firm* — Duane Morris LLP; Gregory M. Lefkowitz; Brandon A. Chan

(57) ABSTRACT

An emollient composition comprising at least one hydrocarbon fluid in an amount of 50 to 100% by weight relative to the total weight of the composition is provided. The fluid can be obtained by a process of catalytically hydrogenating a feed comprising more than 85% by weight of oligomerized olefins, at a temperature from 115 to 195° C. and at a pressure from 30 to 70 bars. A cosmetic, dermatological or pharmaceutical composition comprising the emollient composition and uses thereof are also provided.

11 Claims, No Drawings

EMOLLIENT COMPOSITION

CROSS-REFERENCE TO RELATED APPLICATIONS

This application is a divisional of U.S. Utility application Ser. No. 16/481,017, filed Jul. 25, 2019, which is a § 371 national stage entry of International Application No. PCT/EP2018/053472, filed on Feb. 13, 2018, which claims priority to European Patent Application No. 17155898.4, filed on Feb. 13, 2017, the entire contents of which are incorporated herein by reference.

FIELD OF THE INVENTION

The invention relates to a novel emollient composition, and especially one emollient composition in which the isododecane is obtained by a specific hydrogenation process.

The invention also relates to a cosmetic, dermatological or pharmaceutical composition comprising said emollient composition and its use.

The present invention also relates to the use of said emollient composition for the formulation of cosmetic products, dermatological products or pharmaceutical products.

BACKGROUND ART

The emollients currently used in cosmetics are isoparaffins derived from petrochemicals (mainly isododecane and isohexadecane), white oils, silicone oils or oils based on esters (synthetic or natural). Isoparaffins, white oils and silicone oils are widely distributed because they are very stable and odorless. Isododecane is one of the emollients most often used. However, isododecane is not readily available today and is subject to shortage.

Hence, it would be of interest to have an alternate emollient being of isoparaffinic nature, having properties similar if not identical to those of isododecane, and which could be prepared by a process readily available.

SUMMARY OF THE INVENTION

The invention provides an emollient composition comprising at least one hydrocarbon fluid in an amount of 50 to 100% by weight, preferably from 80 to 100% by weight, more preferably from 90 to 100% by weight and preferably equal to 100% by weight relative to the total weight of the composition, said fluid being obtainable by a process of catalytically hydrogenating a feed comprising more than 85% by weight, preferably more than 90% by weight of oligomerized olefins, at a temperature from 115 to 195° C. and at a pressure from 30 to 70 bars.

According to one embodiment, the hydrocarbon fluid has a brome Index of less than 5, preferably less than 2, more preferably less than 1 mgBr/100 g of fluid.

According to one embodiment, the process of catalytically hydrogenating comprises three hydrogenation stages, preferably in three separate reactors.

According to one embodiment, the feed comprises more than 90% by weight of oligomerized olefins, most preferably more than 95% by weight of oligomerized olefins, and preferably a majority of C12 olefins.

According to another embodiment, the feed is selected from trimeric butene (also named trimeric butylene) and tetrameric propylene (also named tetrameric propene) cuts.

According to another embodiment, the hydrogenation conditions are the following:

Pressure: 40 to 60 bars, and preferably at about 50 bars;
Temperature: 125 to 185° C. and preferably 135 to 175° C.;
Liquid hourly space velocity (LHSV): 0.1 to 3 $hr^{-1}$, preferably 0.2 to 2 $hr^{-1}$, and most preferably 0.3 to 1 $hr^{-1}$;
Hydrogen treat rate: 50 to 300 $Nm^3$/ton of feed, preferably 60 to 200 $Nm^3$/ton of feed and most preferably 80 to 130 $Nm^3$/ton of feed.

According to another embodiment, the process comprises (i) a fractionating step which is carried out before the hydrogenating step, or after the hydrogenating step or both, or (ii) the process comprises three hydrogenation stages, preferably in three separate reactors, or (iii) both (i) and (ii).

According to another embodiment, the fluid contains less than 50 ppm of aromatics by weight, preferably less than 20 ppm by weight, more preferably less than 10 ppm by weight.

According to another embodiment, the fluid contains more than 80% by weight of isoparaffins, preferably more than 85% by weight of isoparaffins and more preferably more than 90% by weight of isoparaffins, and advantageously the fluid contains more than 97% by weight, preferably more than 98% by weight of C12 isoparaffin.

According to another embodiment, the fluid has a boiling point from 170 to 220° C., preferably from 180 to 210° C., and/or wherein the fluid has a boiling range below 80° C., preferably not more than 60° C., more preferably not more than 40° C., advantageously from 10 to 20° C.

The invention further provides a cosmetic, dermatological or pharmaceutical composition comprising at least one emollient composition according to the invention, preferably in an amount ranging from 0.5 to 80%, preferably from 1 to 50% and preferably 5 to 30% by weight relative to the total weight of the composition, preferably of an emollient composition comprising 100% fluid.

According to one embodiment, the cosmetic, dermatological or pharmaceutical composition above comprises at least one fatty substance selected from vegetable oils, hydrocarbon oils other than hydrocarbon oil of said emollient composition, vegetable butters, fatty ethers and alcohols, oily esters, alkanes and silicone oils and/or at least one additive.

According to another embodiment, the cosmetic, dermatological or pharmaceutical composition above which is an anhydrous composition, an emulsion such as a water-in-oil emulsion (W/O), an oil-in-water emulsion (O/W) or a multiple emulsion (including W/O/W or O/W/O), a nano-emulsion, or a dispersion.

The invention also provides the cosmetic use of the compositions of the invention for topical application, in particular as a care product for the skin, such as make-up product, as hair product, like makeup remover, such as scented product, as sunscreen.

The invention also provides the compositions of the invention for pharmaceutical use.

The invention also provides the use of the emollient compositions according to the invention for the preparation of cosmetic, dermatological or pharmaceutical products.

The invention also provides the process for the cosmetic treatment of the skin comprising at least a step of applying, preferably by spreading, the emollient compositions according to the invention.

DESCRIPTION OF EMBODIMENTS OF THE INVENTION

The invention relates to an emollient composition comprising a fluid obtained by a specific process, where in a preferred embodiment said fluid being substitutable with isododecane.

The process provides a fluid for use in the invention is the process which is for preparing a fluid having a boiling point in the range of from 150 to 260° C., preferably from 150 to 230° C. and comprising more than 80% of isoparaffins and less than 50 ppm of aromatics, comprising the step of catalytically hydrogenating a feed comprising more than 85% by weight, preferably more than 90% by weight of oligomerized olefins, at a temperature from 115 to 195° C. and at a pressure from 30 to 70 bars.

In the preferred embodiment the process comprises the step of catalytically hydrogenating a feed comprising more than 90% by weight of oligomerized olefins, at a temperature from 115 to 195° C. and at a pressure from 30 to 70 bars. The feed is a specific feed, as is disclosed below.

The feedstock will first be disclosed, then the hydrogenation step and the associated fractionating step, and finally the fluids.

Feed

The feedstock or simply feed is a feed which is the result of a process of oligomerization of olefins, as practised in the petrochemical field.

The oligomerization process applied transforms olefins contained in light cracked cuts into heavier olefins containing more than 6 carbon atoms (also called C6+ olefins).

Various oligomerization processes are discloses in the literature. Most of these processes are for production of iso-olefins oligomers.

US2005/0288471 discloses a process for the production of oligomers of 1- or 2- butane, in particular octenes and dodecenes, from a hydrocarbon stream consisting of branched and linear hydrocarbon compounds having 4 carbon atoms and comprising olefinic branched and linear hydrocarbons compounds having 4 carbon atoms. This process enables the preparation of substantially unbranched octene and dodecene from a fraction comprising both linear and branched olefinic hydrocarbon compounds having 4 carbon atoms.

In the Polynaptha™ process developed by Axens, propylene and/or mixed butenes are catalytically oligomerized in a series of fixed bed reactors. Conversion and selectivity are controlled by reactor temperature adjustment while the heat of reaction is removed by feed-effluent heat exchange and intermediate reactor cooling. The reactor section effluent is fractionated producing LPG raffinate, gasoline and middle distillate fractions such as kerosene or diesel. This technology is well suited for revamping existing phosphoric acid polymerization units.

Another possible process for the production of olefins is the Selectopol™ process from Axens. This process is a variant of the Polynaphtha™ process using the same catalyst but at lower severity.

Light olefin conversion ranges typically from 90 to 99% depending on feedstock quality and product distribution.

Such feed is also called olefinic cut. The olefinic cut used as feed for the process of the invention contains less than 5% by weight of paraffins, preferably less than 2% and more preferably less than 1%.

The olefinic cut used as feed for the process of the invention contains more than 90% by weight of olefins, preferably more than 92%, more preferably more than 95% measured according to ASTM D1319.

The feed typically contains less than 2 ppm by weight of sulphur, preferably less than 1 ppm by weight and more preferably less than 0.5 ppm by weight measured according to NF M 07059.

The feed typically contains also less than 10% by weight of aromatics, preferably less than 8% and more preferably less than 5% measured by HPLC (EN ISO 12916).

The feed typically has a boiling point in the range of from 170 to 280° C., preferably from 180 to 250° C. and more preferably from 180 to 220° C. according to EN ISO 3405.

Typically, the feed shall have a density at 15° C. lower than or equal to 0.800 g/cm3 as measured according to method ASTM D4052.

According to one embodiment, the feed shall have a density lower or equal to 0.800 g/cm3 as measured according to method ASTM D4052, and it should consist mostly of an olefinic cut with a boiling point in the range of from 170 to 280° C.

According to another embodiment, the feed contains less than 2 ppm by weight of sulphur and less than 10% of aromatics. Preferably, the feed contains less than 1 ppm by weight of sulphur and less than 8% of aromatics. More preferably, the feed contains less than 0.5 ppm of sulphur and less than 5% of aromatics.

According to another embodiment, the feed contains less than 5% by weight of paraffins, more than 90% of olefins and less than 10% of aromatics. Preferably, the feed contains less than 2% by weight of paraffins, more than 92% of olefins and less than 8% of aromatics. More preferably the feed contains less than 1% by weight of paraffins, more than 95% of olefins and less than 5% of aromatics.

According to another embodiment, the feed consists of an olefinic cut comprising a majority of $C_{12}$ olefins.

The most preferred embodiment is one where the feed consists of an olefinic cut comprising a majority of branched (iso) $C_{12}$ olefins chosen amongst trimeric butene cuts and tetrameric propylene cuts.

According to another embodiment, the feed consists of a trimeric butene cut, also called tri-n-butene cutwith a boiling range of from 170 to 260° C.

According to another embodiment, the feed consists of a tetrameric propylene cut with a boiling range from 150 to 260° C.

Preferably, within the meaning of the present invention, the expression "a majority of" means "more than 50% by weight, preferably at least 70% by weight, more preferably at least 90% by weight, even more preferably at least 95% by weight".

As indicated above this specific feed typically contains less than 2 ppm by weight of sulphur, preferably less than 1 ppm by weight and more preferably less than 0.5 ppm by weight measured according to NF M 07059.

Such feeds are readily available; they can be produced for example according to the references cited above, including US2005/0288471, the Polynaptha™ process, and the variant Selectopol™ process from Axens.

Hydrogenation Step

The feedstock issued from the oligomerization of olefins is then hydrogenated. Preferably the feedstock issued from the oligomerization of olefins is a trimeric butene cut and ideally a tri-n-butene cut comprising a majority of 12 carbon atoms olefins. The feedstock can optionally be pre-fractionated.

The hydrogenation step allows the conversion of olefins to paraffins and the elimination of almost all the aromatics compounds. The process of the invention is particularly efficient to convert the (normal and/or iso) olefin cut into low aromatics iso-paraffinic fluids.

Hydrogen that is used in the hydrogenation unit is typically a high purity hydrogen, e.g. with a purity of more than 99%, albeit other grades can be used.

Hydrogenation takes place in one or more reactors. The reactor can comprise one or more catalytic beds. Catalytic beds are usually fixed beds.

Hydrogenation takes place using a catalyst. Typical hydrogenation catalysts include but are not limited to: nickel, platinum, palladium, rhenium, rhodium, nickel tungstate, nickel molybdenum, molybdenum, cobalt molybdenate, nickel molybdenate on silica and/or alumina carriers or zeolites. A preferred catalyst is Ni-based and is supported on an alumina carrier, having a specific surface area varying from 100 to 200 m$^2$/g of catalyst.

The hydrogenation conditions are typically the following:
Pressure: 30 to 70 bars, preferably 40 to 60 bars, and most preferably at about 50 bars;
Temperature: 115 to 195° C., preferably 125 to 185° C. and most preferably 135 to 175° C.;
Liquid hourly space velocity (LHSV): 0.1 to 3 hr$^{-1}$, preferably 0.2 to 2 hr$^{-1}$, and most preferably 0.3 to 1 hr$^{-1}$;
Hydrogen treat rate: 50 to 300 Nm$^3$/ton of feed, preferably 60 to 200 Nm$^3$/ton of feed and most preferably 80 to 130 Nm$^3$/ton of feed.

The temperature in the reactors can be typically about 150-160° C. and the pressure can be typically about 50 bars while the liquid hourly space velocity can be typically about 0.6 and the treat rate can be typically about 80 to 130 Nm$^3$/ton of feed, depending on the feed quality.

The hydrogenation process of the invention can be carried out in several stages. There can be two or three stages, preferably three stages, preferably in three separate reactors. The first stage will operate the sulphur trapping, hydrogenation of substantially all unsaturated compounds, and up to about 90% of hydrogenation of aromatics. The flow exiting from the first reactor contains substantially no sulphur. In the second stage the hydrogenation of the aromatics continues, and up to 99% of aromatics are hydrogenated. The third stage is a finishing stage, allowing an aromatic content as low as 300 ppm or even less such as below 100 ppm or even below 50 ppm. The third stage may allow reducing the bromine index to a value of less than 5 mgBr/100 g of fluid or even less such as below 2 or even below 1 mgBr/100 g of fluid. The catalysts can be present in varying or substantially equal amounts in each reactor, e.g. for three reactors according to weight amounts of 0.05-0.5/0.10-0.70/0.25-0.85, preferably 0.07-0.25/0.15-0.35/0.4-0.78 and most preferably 0.10-0.20/0.20-0.32/0.48-0.70.

It is also possible to have two hydrogenation reactors instead of three.

It is also possible that the first reactor be made of twin reactors operated alternatively in a swing mode. This may be useful for catalyst charging and discharging: since the first reactor comprises the catalyst that is poisoned first (substantially all the sulphur is trapped in and/or on the catalyst) it should be changed often.

One reactor can be used, in which two, three or more catalytic beds are installed.

It may be necessary to insert quenches on the recycle to cool effluents between the reactors or catalytic beds to control reaction temperatures and consequently hydrothermal equilibrium of the hydrogenation reaction. In a preferred embodiment, there is no such intermediate cooling or quenching.

In an embodiment the resulting product and/or separated gas is/are at least partly recycled to the inlet of the hydrogenation stages. This dilution helps maintaining the exothermicity of the reaction within controlled limits, especially at the first stage. Recycling also allows heat-exchange before the reaction and also a better control of the temperature. The stream exiting the hydrogenation unit contains the hydrogenated product and hydrogen. Flash separators are used to separate effluents into gas, mainly remaining hydrogen, and liquids, mainly hydrogenated hydrocarbons. The process can be carried out using three flash separators, one of high pressure, one of medium pressure, and one of low pressure, very close to atmospheric pressure.

The hydrogen gas that is collected on top of the flash separators can be recycled to the inlet of the hydrogenation unit or at different levels in the hydrogenation units between the reactors.

The fractionation stage can be carried out at about atmospheric pressure, or it can be carried out under vacuum pressure that is at about from 10 to 50 mbars, more preferably from 20 to 40 mbars, even more preferably at about 30 mbars.

The fractionation stage can be operated such that various hydrocarbon fluids can be withdrawn simultaneously from the fractionation column, and the boiling range of which can be predetermined.

Therefore, fractionation can take place before hydrogenation, after hydrogenation, or both.

The hydrogenation reactors, the separators and the fractionation unit can thus be connected directly, without having to use intermediate tanks. By adapting the feed, especially the initial and final boiling points of the feed, it is possible to produce directly, without intermediate storage tanks, the final products with the desired initial and final boiling points. Moreover, this integration of hydrogenation and fractionation allows an optimized thermal integration with reduced number of equipment and energy savings.

Fluid used in the Invention

The fluids of the invention, produced according to the process of the invention possess outstanding properties, in terms of aniline point or solvency power, molecular weight, vapour pressure, viscosity, defined evaporation conditions, and defined surface tension. Moreover the fluids of the invention are odourless and have a low pour point.

The fluids resulting of the hydrogenating process of the invention are isoparaffinic fluids with very low aromatics content.

Typically, the isoparaffinic fluids of the invention comprise from 11 to 13 carbon atoms, preferably 12 carbon atoms.

The isoparaffinic fluids of the invention have a boiling point in the range of from 150 to 260° C. according to ASTM D86, preferably from 150 to 230° C., more preferably from 170 to 220° C. and even more preferably from 180 to 210° C. and also exhibit an enhanced safety, due to the very low aromatics content.

The boiling range of the improved fluids is preferably not more than 90° C., preferably not more than 80° C., more preferably not more than 60° C., even more preferably not more than 40° C., advantageously from 10 to 20° C.

The fluids of the invention are paraffinic fluids. They contain typically more than 90% by weight of paraffins, preferably more than 93% by weight of paraffins and even more preferably more than 97% by weight of paraffins, as measured by gas chromatography GC.

The fluids of the invention are primarily isoparaffinic and contain more than 80% by weight of isoparaffins, preferably more than 85% by weight of isoparaffins and more preferably more than 90% by weight of isoparaffins measured by GC. These fluids can be qualified as isoparaffinic fluids.

The fluids of the invention contain less than 10% by weight of normal paraffins, preferably less than 8% by weight of normal paraffins and more preferably less than 5% by weight of normal paraffins measured by GC.

The fluids of the invention contain less than 10% by weight of naphthens, preferably less than 7% by weight of naphthens and more preferably less than 3% by weight of naphthens measured by GC.

The isoparaffinic fluids of the invention or simply the fluids of the invention typically contain less than 50 ppm by weight of aromatics measured by UV spectrometry, more preferably less than 20 ppm, and even more preferably less than 10 ppm. This makes them suitable for use in construction fluids compositions as well as in industrial products.

According to one embodiment the isoparaffinic fluids of the invention contain more than 80% by weight of isoparaffins, less than 10% by weight of naphthens and less than 50 ppm of aromatics. Preferably, the isoparaffinic fluids of the invention contain more than 85% by weight of isoparaffins, less than 7% by weight of naphthens and less than 20 ppm of aromatics. More preferably, the isoparaffinic fluids of the invention contain 90% by weight of isoparaffins, less than 3% by weight of naphthens and less than 10 ppm of aromatics.

According to a second embodiment the isoparaffinic fluids of the invention contain more than 80% by weight of isoparaffins, less than 10% by weight of normal paraffins, less than 10% by weight of naphthens and less than 50 ppm of aromatics. Preferably, the isoparaffinic fluids of the invention contain more than 85% by weight of isoparaffins, less than 8% by weight of normal paraffins, less than 7% of by weight naphthens and less than 20 ppm of aromatics. More preferably, the isoparaffinic fluids of the invention contain 90% by weight of isoparaffins, less than 5% by weight of normal paraffins, less than 3% by weight of naphthens and less than 10 ppm of aromatics.

According to another embodiment the isoparaffinic fluids of the invention contain more than 80% by weight of isoparaffins, less than 10% by weight of normal paraffins, less than 10% by weight of naphthens, less than 50 ppm of aromatics and have a boiling point in the range of from 150 to 260° C., preferably from 150 to 230° C. Preferably, the isoparaffinic fluids of the invention contain more than 85% by weight of isoparaffins, less than 8% by weight of normal paraffins, less than 7% by weight of naphthens, less than 20 ppm of aromatics and have a boiling point in the range of from 170 to 220° C. More preferably, the isoparaffinic fluids of the invention contain 90% by weight of isoparaffins, less than 5% by weight of normal paraffins, less than 3% by weight of naphthens and less than 10 ppm of aromatics and have a boiling point in the range of from 180 to 210° C.

The isoparaffinic fluids of the invention also have extremely low sulphur content, typically less than 5 ppm by weight, even less than 3 ppm and preferably less than 1 ppm, at a level too low to be detected by the usual low-sulphur analyzers.

The isoparaffinic fluids of the invention also have an aniline point from 70 to 90° C., preferably from 75 to 85° C., more preferably at 82° C. according to ISO 2977.

The isoparaffinic fluids of the invention also have a pour point below −50° C., preferably below −60° C. according to ASTM D97.

The isoparaffinic fluids of the invention preferably have a brome Index of less than 5, preferably less than 2, more preferably less than 1 mgBr/100 g of fluid, according to ASTM D 2710.

All percentages and ppm are by weight unless indicated to the contrary. Singular and plural are used interchangeably to designate the fluid(s).

The most preferred fluid of the invention, produced according to the process of the invention starting from the most preferred feed possess properties almost identical to the ones of the isododecane, and is a substitute therefor. It is odourless and has evaporation rate substantially identical to the isododecane. The sensorial properties, as assessed by a panel of users, are substantially identical to the ones of isododecane.

The boiling range of the most preferred fluid is preferably from 10 to 20° C.

The fluids of the invention provide emollient compositions; especially the most preferred fluid provide emollient compositions similar to emollient compositions made from isododecane.

The emollient compositions comprising the fluid will now be described.

Miscibility of the Emollient Composition.

In addition to its physicochemical properties and sensorial properties close to those of isododecane due to the intrinsic composition of the hydrocarbon oil, the emollient composition of the invention has a very good miscibility with other fats conventionally used in cosmetic, dermatological or pharmaceutical fields.

In particular, the emollient composition of the invention has a good miscibility with fats selected from the group consisting of: hydrocarbon oils of biological or petrochemical origin (other than hydrocarbon oil of said emollient composition), vegetable oils, vegetable butters, fatty ethers and alcohols, oily esters, alkanes and silicone oils.

The hydrocarbon oils are fats from petrochemical processes. For example, there may be mentioned mineral oils, isoparaffins, waxes, paraffins, polyisobutenes or polydecenes.

Examples of vegetable oils include wheat germ oil, sunflower oil, grape seed, sesame, maize, apricot, castor, shea butter, avocado, olive, soybean, sweet almond oil, palm oil, rapeseed, cotton, hazelnut, macadamia, jojoba, alfalfa, poppy, pumpkin, sesame, cucumber, rapeseed, blackcurrant, evening primrose, millet, barley, quinoa, rye, safflower, aleurite molucana, passionflower or musk rose camellia.

Vegetable butters are fatty substances that have the same properties as vegetable oils. The difference between both lies in the fact that the butters are in solid form at room temperature. Also, unlike the vegetable oils, the raw material from which is extracted a butter (pulp, seeds or almonds) is heated after having been milled for extracting the fat. As vegetable oils, butters can be refined to ensure better conservation, neutralize odors, improve the color and consistency. Being rich in antioxidants and nourishing, vegetable butters have cosmetic properties of enhancing skin elasticity, protect from external aggression by leaving a protective film on the skin and reducing dehydration, repair and soothe by regenerating the natural hydrolipidic film on the skin. Examples of vegetable butters include shea butter, cocoa butter, mango butter, chorea butter or butter olive.

Ethers and fatty alcohols are fatty waxy substances with long chains and with remarkable properties including film forming, emollient, moisturizing, softening and protective. They act as moisturizing oils and as emulsifiers. Fatty alcohol ethers or examples are: cetyl alcohol, the stearyl alcohol, myristyl alcohol, the auryl alcohol, the behenyl alcohol, the cetearyl alcohol, the ethers dicaprylyl, ethers or stearyl octyldodecanol (identified by their INN).

Oily esters or ester oils are the product of a reaction between fatty acids (longer-chain acids, such as stearic acid, oleic acid, palmitic acid) and alcohols (fatty alcohols or polyols such as glycerol). These oils may contain substances derived from petrochemicals, as is the case for Isopropyl Palmitate. Examples of oily esters are caprylic capric triglyceride, coconut caprylate caprate, oleyl erucate, oleyl linoleate, decyl oleate or PPG-3 Benzyl ether myristate (identified by their INN).

The term polysiloxanes or silicone oils, an oil comprising at least one silicon atom, and in particular at least one Si—O group. As silicone oil, mention may be made the phenylpropyldimethylsiloxysilicate, dimethicones or on the cyclopentasiloxane (identified by their INN).

Additives.

The emollient composition according to the invention can also be mixed with any adjuvant or additive commonly used in the fields considered, particularly in the cosmetic, dermatological or pharmaceutical. The skilled man will select the optional additives of the composition according to the invention such that the advantageous properties intrinsically associated with the emollient composition according to the invention are not, or not substantially impaired by the addition envisaged. Among the conventional additives which may be present (based on water-soluble or liposoluble nature of these adjuvants) are included in particular the foaming surfactants such as anionic surfactant (such as sodium lauryl ether sulfate, sodium alkyl phosphate, trideceth sodium sulfate), amphoteric surfactant (such as alkyl betaine, disodium cocoamphodiacetate) or nonionic surfactant of HLB 10 (such as POE/PPG/POE alkylpolyglucoside, polyglyceryl-3hydroxylauryl ether); conservatives; sequestering agents (EDTA); antioxidants; perfumes; colorants such as soluble dyes, pigments and nacres; mattifying fillers, tensioning agents, bleaching agents or exfoliants; sunscreens; cosmetic or dermatological active agents and having the effect of improving the cosmetic properties of the skin, whether hydrophilic or lipophilic; electrolytes; hydrophilic or lipophilic, anionic, nonionic, cationic or amphoteric polymers; thickeners, gelling agents or dispersing agents. The amounts of these various adjuvants are those conventionally used in the field, for example from 0.01 to 20% of the total weight of the composition. Active agents used in the emollient composition of the invention include for example, water-soluble or liposoluble vitamins such as vitamin A (retinol), vitamin E (tocopherol), vitamin C (ascorbic acid), vitamin B5 (panthenol), vitamin B3 (niacinamide), derivatives of these vitamins (especially esters) and mixtures thereof; antiseptics; antibacterial active such as 2,4,4'-trichloro-2'-hydroxy ether (or triclosan), 3,4,4'-trichlorocarbanilide (or triclocarban); antiseborrhoeics; antimicrobial agents such as benzoyl peroxide, niacin (vitamin PP); slimming agents such as caffeine; optical brighteners, and any active principle appropriate for the final purpose of the composition, and mixtures thereof.

Composition.

The present invention therefore also relates to a cosmetic, dermatological or pharmaceutical composition comprising the emollient composition described above, at least one fatty substance chosen from: plant oils, vegetable butters, fatty ethers and alcohols, oily esters, alkanes and silicone and at least one additive chosen from the abovementioned additives oils.

The cosmetic, dermatological or pharmaceutical comprises a physiologically acceptable medium, i.e. which does not have deleterious side effects and in particular which does not produce redness, overheating, tautness or stinging unacceptable for the user. The medium optionally comprises water and/or at least one oil as fat, in addition to the aforementioned emollient composition.

According to one embodiment, the cosmetic, dermatological or pharmaceutical composition has an emollient content as described ranging from 0.5 to 80%, preferably 1 to 50% and preferably 5 to 30% by weight based on the weight total composition. The cosmetic, dermatological or pharmaceutical composition according to the invention may thus be an anhydrous composition, an emulsion such as a water-in-oil emulsion (W/O), an oil-in-water emulsion (O/W) or a multiple emulsion (including W/O/W or O/W/O), a nano-emulsion, or a dispersion.

The cosmetic, dermatological or pharmaceutical composition according to the invention is in the form of more or less soft cream or vaporizable emulsion, it may constitute for example a composition for removing makeup or cleaning the skin, lips, an sun composition (UV protection), or after-sun, a composition for skin massage, a shower care balm composition, an antiperspirant composition, a mask composition, a refreshing balm composition, an composition which is scrubbing and/or exfoliating for both the face and the hands (when it contains exfoliating particles), a makeup composition, a shaving composition, an aftershave balm composition, a fragrant composition, a composition for wipes or a vaporizable composition.

The composition of the invention is advantageously characterized in that it has a stability that is similar to the one of composition based on traditional isododecane.

Use of the Emollient Composition.

The invention also relates to the cosmetic, dermatological or pharmaceutical use of the composition of the invention for topical application.

The invention also relates to the cosmetic, dermatological or pharmaceutical use as a skin care product (serums, creams, balms, etc.), as a hygiene product, such as sun product/after-sun, as make-up product such as makeup remover, such as scented product, as antiperspirant product.

The invention also relates to a cosmetic, dermatological or pharmaceutical skin treatment, comprising at least one step of applying to the skin a composition as defined above.

The composition of the invention can also be used for the preparation of cosmetic compositions, dermatological compositions or pharmaceutical compositions, comprising other components or phases other than those described above. It may include the formulation of care compositions, hygiene compositions, make-up composition.

Cosmetic Treatment Process.

Finally, the invention also covers a cosmetic treatment method comprising at least a step of applying, preferably by spreading, on the skin of the compositions according to the invention.

All percentages and ppm are by weight unless indicated to the contrary. Singular and plural are used interchangeably to designate the fluid(s).

EXAMPLES

The following examples illustrate the invention without limiting it.

Example 1

In the present invention, a commercial trimeric butene feedstock, typically a C12-centered iso-olefinic cut, was hydrogenated in presence of a nickel hydrogenating catalyst according to the process of the invention under a pressure of 50 bars, at a liquid hourly space velocity (LHSV) of 0.6 h$^{-1}$ and at a temperature from 135 to 175° C.

The table 1 shows the characteristics of the trimeric n-butene feedstock.

TABLE 1

| Analyses | Normes | Unit | Values |
|---|---|---|---|
| Density at 15° C. | EN ISO 12185 | kg/m3 | 771.0 |
| Aromatic content | HPLC (EN ISO 12916) | % | <5 |
| Paraffinic content | FIA ASTM D1319 | % | <0.3 |
| Olefin content | FIA ASTM D1319 | % | >95 |
| Bromine number | ASTN D 1159 | g Br2/100 g | 98.0 |
| Sulfur content | NF M 07059 | ppm | 0.1 |
| Distillation D86 | Normes | Unités | |
| Initial Point | EN ISO 3405 | ° C. | 192.2 |
| 2% Point | EN ISO 3405 | ° C. | 195.3 |
| 5% Point | EN ISO 3405 | ° C. | 195.6 |
| 10% Point | EN ISO 3405 | ° C. | 195.7 |
| 20% Point | EN ISO 3405 | ° C. | 196.0 |
| 30% Point | EN ISO 3405 | ° C. | 196.2 |
| 40% Point | EN ISO 3405 | ° C. | 196.4 |
| 50% Point | EN ISO 3405 | ° C. | 196.6 |
| 60% Point | EN ISO 3405 | ° C. | 196.9 |
| 65% Point | EN ISO 3405 | ° C. | 197.1 |
| 70% Point | EN ISO 3405 | ° C. | 197.2 |
| 80% Point | EN ISO 3405 | ° C. | 197.8 |
| 90% Point | EN ISO 3405 | ° C. | 198.9 |
| 95% Point | EN ISO 3405 | ° C. | 200.6 |
| Dry Point | EN ISO 3405 | ° C. | 205.4 |

The hydrogenation process is carried out and the hydrogenated cut is then fractionated into different cuts, the main one showing the characteristics given in table 2 hereafter.

TABLE 2

| Analyses | Norms | Unity | Isoparaffinic hydrogenated distillate |
|---|---|---|---|
| Density at 15° C. | EN ISO 12185 | kg/m3 | 768.0 |
| Appearance | VISUAL | — | clear & bright |
| Saybolt Colour | NF M 07-003 | — | 30 |
| Refractive index at 20° C. | ASTM D 1218 | — | 1.4278 |
| Pensky-Martens Flash Point | EN ISO 2719 | ° C. | 70.5 |
| Viscosity at 20° C. | EN ISO 3104 | mm2/s | 1.754 |
| Viscosity at 40° C. | EN ISO 3104 | mm2/s | 1.285 |
| Aniline Point | ISO 2977 | ° C. | 79.3 |
| Paraffinic content | GC | % | 97.34 |
| Iso-paraffin content | GC | % | 94.25 |
| Normal paraffin content | GC | % | 3.09 |
| Naphtenic content | GC | % | 2.66 |
| Aromatic content | UV spectrometry | ppm | 8 |
| Brome Index | ASTM D 2710 | mgBr/100 g | 0 |
| Benzene content | ASTM D 6229 | ppm | 0 |
| Sulfur content | NF M 07059 | ppm | <0.1 |
| Distillation D86 | — | — | — |
| Initial Point | EN ISO 3405 | ° C. | 192.3 |
| 2% Point | EN ISO 3405 | ° C. | 194.2 |
| 5% Point | EN ISO 3405 | ° C. | 194.6 |
| 10% Point | EN ISO 3405 | ° C. | 194.8 |
| 20% Point | EN ISO 3405 | ° C. | 195.1 |
| 30% Point | EN ISO 3405 | ° C. | 195.3 |
| 40% Point | EN ISO 3405 | ° C. | 195.5 |
| 50% Point | EN ISO 3405 | ° C. | 195.7 |
| 60% Point | EN ISO 3405 | ° C. | 195.8 |
| 65% Point | EN ISO 3405 | ° C. | 195.9 |
| 70% Point | EN ISO 3405 | ° C. | 196.1 |
| 80% Point | EN ISO 3405 | ° C. | 196.5 |
| 90% Point | EN ISO 3405 | ° C. | 197.6 |
| 95% Point | EN ISO 3405 | ° C. | 200.2 |
| Dry Point | EN ISO 3405 | ° C. | 206.8 |

If needed, further treatments can bring the C12 isoparaffin level to values higher than 97%, even higher than 98%.

When applied on the skin, the oil exhibits sensorial properties and evaporation rate substantially similar to those of the isododecane. The resulting hydrocarbon oil has thus properties making it a substitute for isododecane.

Example 2

A tetrameric propylene feedstock, typically a C12-centered iso-olefinic cut, was hydrogenated with the same experimental conditions as the trimeric butylene cut feedstock in example 1.

Table 3 shows the characteristics of the tetrameric propylene feedstock.

TABLE 3

| Analyses | Norms | Unit | Values |
|---|---|---|---|
| Density at 15° C. | EN ISO 12185 | kg/m$^3$ | 777.2 |
| Aromatic content | HPLC (EN ISO 12916) | % | <5 |
| Paraffinic content | FIA ASTM D1319 | % | <0.3 |
| Olefin content | FIA ASTM D1319 | % | >95 |
| Bromine Number | ASTM D 2710 | gBr$_2$/100 g | 95 |
| Sulfur content | NF M 07059 | ppm | 0.1 |
| Distillation D86 | | | |
| Initial Point | EN ISO 3405 | ° C. | 174.5 |
| 1% Point | EN ISO 3405 | ° C. | 178.3 |
| 2% Point | EN ISO 3405 | ° C. | 180.0 |
| 5% Point | EN ISO 3405 | ° C. | 183.1 |
| 10% Point | EN ISO 3405 | ° C. | 185.6 |
| 20% Point | EN ISO 3405 | ° C. | 188.9 |
| 30% Point | EN ISO 3405 | ° C. | 192.0 |
| 40% Point | EN ISO 3405 | ° C. | 195.2 |
| 50% Point | EN ISO 3405 | ° C. | 198.1 |
| 60% Point | EN ISO 3405 | ° C. | 201.5 |
| 65% Point | EN ISO 3405 | ° C. | 203.4 |
| 70% Point | EN ISO 3405 | ° C. | 205.6 |
| 80% Point | EN ISO 3405 | ° C. | 211.8 |
| 90% Point | EN ISO 3405 | ° C. | 223.9 |
| 95% Point | EN ISO 3405 | ° C. | 234.3 |
| Dry Point | EN ISO 3405 | ° C. | 252.7 |

The hydrogenation process is carried out and the hydrogenated cut is then fractionated into different cuts, the main one showing the characteristics given in table 4 hereafter.

TABLE 4

| Analyses | Norms | Unit | Isoparaffinic hydrogenated distillate |
|---|---|---|---|
| Density at 15° C. | EN ISO 12185 | kg/m$^3$ | 768.9 |
| Appearance | Visual | — | Clear & bright |
| Saybolt Colour | NF M 07-003 | — | 30 |
| Pensky-Martens Flash Point | EN ISO 2719 | ° C. | 67.0 |
| Aromatic content | HPLC (EN ISO 12916) | ppm | 5 |
| Brome index | ASTM D 2710 | mgBr/100 g | 0 |
| Benzene content | ASTM D 6229 | Ppm | 0 |
| Sulfur content | NF M 07059 | ppm | 0.1 |
| Distillation D86 | | | |
| Initial Point | EN ISO 3405 | ° C. | 173.5 |
| 1% Point | EN ISO 3405 | ° C. | 178.7 |
| 2% Point | EN ISO 3405 | ° C. | 180.8 |
| 5% Point | EN ISO 3405 | ° C. | 183.9 |
| 10% Point | EN ISO 3405 | ° C. | 186.7 |
| 20% Point | EN ISO 3405 | ° C. | 190.4 |
| 30% Point | EN ISO 3405 | ° C. | 193.8 |
| 40% Point | EN ISO 3405 | ° C. | 196.9 |
| 50% Point | EN ISO 3405 | ° C. | 200.0 |
| 60% Point | EN ISO 3405 | ° C. | 203.4 |
| 65% Point | EN ISO 3405 | ° C. | 205.6 |

TABLE 4-continued

| Analyses | Norms | Unit | Isoparaffinic hydrogenated distillate |
|---|---|---|---|
| 70% Point | EN ISO 3405 | °C. | 207.8 |
| 80% Point | EN ISO 3405 | °C. | 214.5 |
| 90% Point | EN ISO 3405 | °C. | 227.6 |
| 95% Point | EN ISO 3405 | °C. | 239.3 |
| Dry Point | EN ISO 3405 | °C. | 257.1 |

If needed, further treatments can bring the C12 isoparaffin level to values higher than 97%, even higher than 98%.

When applied on the skin, the oil exhibits sensorial properties and evaporation rate substantially similar to those of the isododecane. The resulting hydrocarbon oil has thus properties making it a substitute for conventional isododecane.

The invention claimed is:

1. A process to prepare an emollient composition, the process comprising:
   a step of preparing a hydrocarbon fluid by a process of catalytically hydrogenating a feed at a temperature from 115 to 195° C. and at a pressure from 30 to 70 bars, wherein the feed consists of a tetrameric propylene cut with a boiling range from 150 to 260° C., wherein the hydrocarbon fluid has a boiling range of at least 10° C. and a bromine index of less than 1 mgBr/100 g of fluid and an aniline point from 70 to 90° C., wherein the fluid contains less than 50 ppm of aromatics by weight,
   wherein the emollient composition comprises from 50 to 100% by weight, relative to the total weight of the composition, of the hydrocarbon fluid.

2. The process of claim 1, wherein the feed comprises more than 90% by weight of oligomerized olefins.

3. The process of claim 1, wherein the hydrogenation conditions are the following:
   Pressure: 40 to 60 bars;
   Temperature: 125 to 185° C.;
   Liquid hourly space velocity (LHSV): 0.1 to 3 hr$^{-1}$; and
   Hydrogen treat rate: 50 to 300 Nm$^3$/ton of feed.

4. The process of claim 1, wherein the catalytically hydrogenating process comprises a fractionating step which is carried out before the hydrogenating step, or after the hydrogenating step or both.

5. The process of claim 1, wherein the fluid contains more than 80% by weight of isoparaffins.

6. The process of claim 1, wherein the fluid has a boiling point from 150 to 260° C., and/or wherein the fluid has a boiling range below 90° C.

7. The process of claim 1, wherein the emollient composition comprises from 90 to 100% by weight of the hydrocarbon fluid, relative to the total weight of the composition.

8. The process of claim 1, wherein the fluid contains more than 97% by weight of C12 isoparaffins.

9. The process of claim 1, wherein the process of catalytically hydrogenating is performed in three hydrogenation stages.

10. The process of claim 1, wherein the process of catalytically hydrogenating is performed in three hydrogenation stages in three separate reactors.

11. The process of claim 1, wherein the emollient composition is used in a cosmetic, dermatological, or pharmaceutical composition, the cosmetic, dermatological, or pharmaceutical composition comprising, relative to the total weight of the composition, at least 50% by weight of the hydrocarbon fluid and further comprises at least one fatty substance selected from vegetable oils, hydrocarbon oils other than the hydrocarbon fluid, vegetable butters, fatty ethers and alcohols, oily esters, alkanes and silicone oils and/or at least one additive.

* * * * *